US008008294B2

(12) United States Patent
Sebhatu et al.

(10) Patent No.: US 8,008,294 B2
(45) Date of Patent: Aug. 30, 2011

(54) CITRATE SALT OF AN INDOLE DERIVATIVE AND ITS PHARMACEUTICAL USE

(75) Inventors: Tesfai Sebhatu, Södertälje (SE); Erica Ståhle, Södertälje (SE)

(73) Assignee: AstraZeneca AB, Sodertalje (SE)

( * ) Notice: Subject to any disclaimer, the term of this patent is extended or adjusted under 35 U.S.C. 154(b) by 439 days.

(21) Appl. No.: 12/162,540

(22) PCT Filed: Jan. 31, 2007

(86) PCT No.: PCT/SE2007/000086
§ 371 (c)(1),
(2), (4) Date: Oct. 1, 2008

(87) PCT Pub. No.: WO2007/089191
PCT Pub. Date: Aug. 9, 2007

(65) Prior Publication Data
US 2009/0023732 A1    Jan. 22, 2009

Related U.S. Application Data

(60) Provisional application No. 60/764,551, filed on Feb. 2, 2006.

(51) Int. Cl.
*A61K 31/5377* (2006.01)
*C07D 413/14* (2006.01)
(52) U.S. Cl. ..................... 514/235.2; 544/124
(58) Field of Classification Search ............... 514/235.2; 544/124
See application file for complete search history.

(56) References Cited

U.S. PATENT DOCUMENTS

| 7,399,780 B2 | 7/2008 | Berg et al. |
| 2007/0203137 A1 | 8/2007 | Sebhatu et al. |

FOREIGN PATENT DOCUMENTS

| JP | 200309588 | 10/2008 |
| WO | 02085897 A1 | 10/2002 |
| WO | 03082853 A1 | 10/2003 |
| WO | 2005027823 | 3/2005 |
| WO | 2006070195 A1 | 7/2006 |

OTHER PUBLICATIONS

Berge et al., "Pharmaceutical Salts", J Pharm Sci 66(1):1-19, 1977.*
Bell, N.H., "Advances in the Treatment of Osteoporosis", Current Drug Targets—Immune, Endocrine & Metabolic Disorders, 2001, vol. 1, pp. 93-102.
Bhat, R. et al, "Regulation and localization of tyrosine etc", PNAS, Sep. 26, 2000, vol. 97, No. 20, pp. 11074-11079.
Cline, G.W. et al, "Effects of a Novel Glycogen Synthase Kinase-3 Inhibitor etc.", Diabetes, Oct. 2002, vol. 51, pp. 2903-2910.
Cotter, D. et al, "Abnormalities of Wnt signalling in schizophrenia—evidence for neurodevelopmental abnormality", NeuroReport 1998, vol. 9, No. 7, pp. 1379-1383.
Gat, U. et al, "De Novo Hair Follicle Morphogenesis and Hair Tumors etc.", Cell, Nov. 25, 1998, vol. 95, pp. 605-614.
Gould, T. et al, "In Vivo Evidence in the Brain for Lithium Inhibition of Glycogen Synthase Kinase-3", Neuropsychopharmacology 2004, vol. 29, pp. 32-38.
Hoshi, M. et al, "Regulation of mitochondrial pyruvate dehydrogenase activity etc.", Proc. Natl. Acad. Sci. USA, Apr. 1996, vol. 93, pp. 2719-2723.
Imahori, K. et al, "Physiology and Pathology of Tau Protein Kinases in Relation to Alzheimer's Disease", J. Biochem. 1997, vol. 121 No. 2, pp. 179-188.
Jope, R.S. et al, "Glycogen Synthase Kinase-3 (GSK3): Inflammation, Diseases, and Therapeutics", Neurochem. Res., Aug. 30, 2006, DOI 10.1007/s11064-006-9128-5.
Klein, P. et al, "A molecular mechanism for the effect of lithium on development", PNAS, Aug. 1996, vol. 93, pp. 8455-8459.
Kozlovsky, N. et al, "Low GSK-3beta Immunoreactivity in Postmortem Frontal Cortex of Schizophrenic Patients", Am. J. Psychiatry, May 2000, 157:5, pp. 831-833.
Li, Xiaohua, et al, "Regulation of mouse brain glycogen synthase kinase-3 etc.", Int. J. of Neuropsychopharmacol, Feb. 2007; 10(1), pp. 7-19. Epub May 4, 2006, doi:10.1017/S1461145706006547.
Martin, M. et al., "Toll-like receptor-mediated cytokine production etc", Nature Immunology, Aug. 2005, vol. 6, No. 8, pp. 777-784.
Nikoulina, S. et al, "Potential Role of Glycogen Synthase Kinase-3 etc", Diabetes, Feb. 2000, vol. 49, pp. 263-271.
O'Brian, W.T. et al, "Glycogen Synthase Kinase etc", The Journal of Neuroscience, Jul. 28, 2004, 24(30), pp. 6791-6798.
Ring, D.B. et al, "Selective Glycogen Synthase Kinase 3 Inhibitors etc.", Diabetes, Mar. 2003, vol. 52, pp. 588-595.
Shusei, et al., "Solid Dispersing Element", Patent Abstracts of Japan, Publication No. 2000-309588, Taisho Pharmaceut Co. Ltd., Filed Apr. 29, 1999.
Stambolic, V. et al, "Lithium inhibits glycogen synthase kinase-3 activity etc.", Current Biology 1996, vol. 6, No. 12, pp. 1664-1668.
Szczepankiewicz, A. et al, "Association Analysis of the GSK-3beta T-50C Gene Polymorphism with Schizophrenia and Bipolar Disorder", Neuropsychobiology, 2006, 53, pp. 51-56.
Su, Y. et al, "Lithium, a Common Drug for Bipolar Disorder Treatment, Regulates etc.", Biochemistry 2004, vol. 43, pp. 6899-6908.
Tobias, J.H., et al, "Novel therapeutic targets in osteoporosis", Expert Opinion Therapeutic Targets 2002, 6(1), pp. 41-56.
Vijayaraghavan et al, "A Role for Phosphorylation of Glycogen Synthase etc", Biology of Reproduction, 2000, 62, pp. 1647-1654.
Patent Abstracts of Japan, Publication No. 2000-309588, Nov. 7, 2000, Taisho Pharmaceut Co. LTD.

* cited by examiner

*Primary Examiner* — Rebecca Anderson
(74) *Attorney, Agent, or Firm* — Kenneth F. Mitchell

(57) ABSTRACT

The salt, the 2-hydroxy-3-[5-(morpholin-4-ylmethyl)pyridin-2-yl]1H-indole-5-carbonitrile citrate, a process for its preparation, pharmaceutical formulations containing it and the use of it in therapy, and particularly in the therapy of GSK3 related conditions and disorders.

8 Claims, No Drawings

CITRATE SALT OF AN INDOLE DERIVATIVE AND ITS PHARMACEUTICAL USE

This is a 371 of International Application number PCT/2007/000086, filed Jan. 31, 2007, which claims the benefit of Provisional Application No. 60/764,551 filed Feb. 2, 2006.

FIELD OF THE INVENTION

The present invention relates to a new pharmaceutically acceptable salt of 2-hydroxy-3-[5-(morpholin-4-ylmethyl)pyridin-2-yl]1H-indole-5-carbonitrile, the 2-hydroxy-3-[5-(morpholin-4-ylmethyl)pyridin-2-yl]1H-indole-5-carbonitrile citrate, a process for its preparation, pharmaceutical formulations containing said salt and to the use of said active salt in therapy.

BACKGROUND OF THE INVENTION

2-Hydroxy-3-[5-(morpholin-4-ylmethyl)pyridin-2-yl]1H-indole-5-carbonitrile as a free base and the hydrochloride salt thereof are described in WO 03/082853. This compound is useful because it possess pharmacological activity by showing inhibiting effect on GSK3 (WO 03/082853). This compound could be used to treat Alzheimer disease, dementias, chronic and acute neurodegenerative diseases, bipolar disorders, schizophrenia, diabetes, hair loss, bone-related disorders and all the listed disorders described in WO 03/082853, which hereby are incorporated into this specification by reference.

Glycogen synthase kinase 3 (GSK3) is a serine/threonine protein kinase composed of two isoforms ($\alpha$ and $\beta$), which are encoded by distinct genes but are highly homologous within the catalytic domain. GSK3 is highly expressed in the central and peripheral nervous system. GSK3 phosphorylates several substrates including tau, $\beta$-catenin, glycogen synthase, pyruvate dehydrogenase and elongation initiation factor 2b (eIF2b). Insulin and growth factors activate protein kinase B, which phosphorylates GSK3 on serine 9 residue and inactivates it.

Alzheimer's Disease (AD) Dementias, and Taupathies.

AD is characterized by cognitive decline, cholinergic dysfunction and neuronal death, neurofibrillary tangles and senile plaques consisting of amyloid-$\beta$ deposits. The sequence of these events in AD is unclear, but is believed to be related. Glycogen synthase kinase 3$\beta$ (GSK3$\beta$) or Tau phosphorylating kinase selectively phosphorylates the microtubule associated protein Tau in neurons at sites that are hyperphosphorylated in AD brains. Hyperphosphorylated tau has lower affinity for microtubules and accumulates as paired helical filaments, which are the main components that constitute neurofibrillary tangles and neuropil threads in AD brains. This results in depolymerization of microtubules, which leads to dying back of axons and neuritic dystrophy. Neurofibrillary tangles are consistently found in diseases such as AD, amyotrophic lateral sclerosis, parkinsonism-dementia of Gaum, corticobasal degeneration, dementia pugilistica and head trauma, Down's syndrome, postencephalatic parkinsonism, progressive supranuclear palsy, Niemann-Pick's Disease and Pick's Disease. Addition of amyloid-$\beta$ to primary hippocampal cultures results in hyperphosphorylation of tau and a paired helical filaments-like state via induction of GSK3$\beta$ activity, followed by disruption of axonal transport and neuronal death (Imahori and Uchida., J. Biochem 121:179-188, 1997). GSK3$\beta$ preferentially labels neurofibrillary tangles and has been shown to be active in pre-tangle neurons in AD brains. GSK3 protein levels are also increased by 50% in brain tissue from AD patients. Furthermore, GSK3$\beta$ phosphorylates pyruvate dehydrogenase, a key enzyme in the glycolytic pathway and prevents the conversion of pyruvate to acetyl-Co-A (Hoshi et al., PNAS 93:2719-2723, 1996). Acetyl-Co-A is critical for the synthesis of acetylcholine, a neurotransmitter with cognitive functions. Accumulation of amyloid-$\beta$ is an early event in AD. GSK Tg mice show increased levels of amyloid-$\beta$ in brain. Also, PDAPP mice fed with Lithium show decreased amyloid-$\beta$ levels in hippocampus and decreased amyloid plaque area (Su et al., Biochemistry 2004, 43:6899-6908). Thus, GSK3$\beta$ inhibition may have beneficial effects in progression as well as the cognitive deficits associated with Alzheimer's disease and other above-referred to diseases.

Chronic and Acute Neurodegenerative Diseases

Growth factor mediated activation of the PI3K/Akt pathway has been shown to play a key role in neuronal survival. The activation of this pathway results in GSK3$\beta$ inhibition. Recent studies (Bhat et. al., PNAS 97:11074-11079 (2000)) indicate that GSK3$\beta$ activity is increased in cellular and animal models of neurodegeneration such as cerebral ischemia or after growth factor deprivation. For example, the active site phosphorylation was increased in neurons vulnerable to apoptosis, a type of cell death commonly thought to occur in chronic and acute degenerative diseases such as cognitive disorders, Alzheimer's Disease, Parkinson's Disease, amyotrophic lateral sclerosis, Huntington's Disease and HIV dementia and traumatic brain injury; and as in ischemic stroke. Lithium was neuroprotective in inhibiting apoptosis in cells and in the brain at doses that resulted in the inhibition of GSK3$\beta$. Thus GSK3$\beta$ inhibitors could be useful in attenuating the course of neurodegenerative diseases.

Bipolar Disorders (BD)

Bipolar Disorders are characterised by manic episodes and depressive episodes. Lithium has been used to treat BD based on its mood stabilising effects. The disadvantage of lithium is the narrow therapeutic window and the danger of overdosing that can lead to lithium intoxication. The discovery that lithium inhibits GSK3 at therapeutic concentrations has raised the possibility that this enzyme represents a key target of lithium's action in the brain (Stambolic et al., Curr. Biol. 6:1664-1668, 1996; Klein and Melton; PNAS 93:8455-8459, 1996; Gould et al., Neuropsychopharmacology, 1:32-8, 2004). GSK3 inhibitor has been shown to reduce immobilisation time in forced swim test, a model to assess on depressive behavior (O'Brien et al., J Neurosci 2004, 24:66791-6798) GSK3 has been associated with a polymorphism found in bipolar II disorder (Szczepankiewicz et al., Neuropsychobiology. 2006;5 3(1):51-6). Inhibition of GSK3$\beta$ may therefore be of therapeutic relevance in the treatment of BD as well as in AD patients that have affective disorders.

Schizophrenia

Accumulating evidence implicates abnormal activity of GSK3 in mood disorders and schizophrenia. GSK3 is involved in signal transduction cascades of multiple cellular processes, particularly during neural development. Kozlovsky et al (Am J Psychiatry 2000 May; 157(5):831-3) found that GSK3$\beta$ levels were 41% lower in the schizophrenic patients than in comparison subjects. This study indicates that schizophrenia involves neurodevelopmental pathology and that abnormal GSK3 regulation could play a role in schizophrenia. Furthermore, reduced $\beta$-catenin levels have been reported in patients exhibiting schizophrenia (Cotter et al., Neuroreport 9:1379-1383 (1998)). Atypical antipsychotics such as olanzapine, clozapine, quetiapine, and ziprasidone, inhibits GSK3 by increasing ser9 phosphorylation suggesting that antipsychotics may exert their beneficial effects via GSK3 inhibition (Rosborough et al., Int J Neuropsychopharmacol, 4:1-13 2006).

Diabetes

Insulin stimulates glycogen synthesis in skeletal muscles via the dephosphorylation and thus activation of glycogen synthase. Under resting conditions, GSK3 phosphorylates and inactivates glycogen synthase via dephosphorylation. GSK3 is also over-expressed in muscles from Type II diabetic patients (Nikoulina et al., Diabetes 2000 February; 49(2): 263-71). Inhibition of GSK3 increases the activity of glycogen synthase thereby decreasing glucose levels by its conversion to glycogen. In animal models of diabetes, GSK3 inhibitors lowered plasma glucose levels up to 50% (Cline et al., Diabetes, 2002, 51:2903-2910; Ring et at., Diabetes 2003, 52:588-595). GSK3 inhibition may therefore be of therapeutic relevance in the treatment of Type I and Type II diabetes and diabetic neuropathy.

Alopecia

GSK3 phosphorylates and degrades β-catenin. β-catenin is an effector of the pathway for keratonin synthesis. β-catenin stabilisation may be lead to increase hair development. Mice expressing a stabilised β-catenin by mutation of sites phosphorylated by GSK3 undergo a process resembling de novo hair morphogenesis (Gat et al., Cell 1998 Nov. 25; 95 (5): 605-14)). The new follicles formed sebaceous glands and dermal papilla, normally established only in embryogenesis. Thus GSK3 inhibition may offer treatment for baldness.

Bone-Related Disorders and Conditions

GSK3 inhibitors could be used for treatment of bone-related disorders or other conditions, which involves a need for new and increased bone formation. Remodeling of the skeleton is a continuous process, controlled by systemic hormones such as parathyroid hormone (PTH), local factors (e.g. prostaglandin $E_2$), cytokines and other biologically active substances. Two cell types are of key importance: osteoblasts (responsible for bone formation) and osteoclasts (responsible for bone resorption). Via the RANK, RANK ligand and osteoprotegerin regulatory system these two cell types interact to maintain normal bone turnover (Bell NH, Current Drug Targets—Immune, Endocrine & Metabolic Disorders, 2001, 1:93-102).

Osteoporosis is a skeletal disorder in which low bone mass and deterioration of bone microarchitecture lead to increased bone fragility and fracture risk. To treat osteoporosis, the two main strategies are to either inhibit bone resorption or to stimulate bone formation. The majority of drugs currently on the market for the treatment of osteoporosis act to increase bone mass by inhibiting osteoclastic bone resorption. It is recognized that a drug with the capacity to increase bone formation would be of great value in the treatment of osteoporosis as well as having the potential to enhance fracture healing in patients.

The use of GSK3 inhibitors in primary and secondary osteoporosis, where primary osteoporosis includes post-menaupausal osteoporosis and senile osteoporosis in both men and women, and secondary osteoporosis includes cortison induced osteoporosis, as well as any other type of induced secondary osteoporosis. In addition to this, GSK3 inhibitors may also be used in treatments of myeloma. The GSK3 inhibitors may be administered locally or systemically, in different formulation regimes, to treat these conditions.

Inflammatory Disease

The discovery that GSK3 inhibitors provide anti-inflammatory effects has raised the possibility of using GSK3 inhibitors for therapeutic intervention in inflammatory diseases. (Martin et al., Nat Immunol 2005, 6:777-784; rev. in Jope et al., Neurochem Res 2006, Aug. 30). Inflammation is a common feature of a broad range of conditions including Alzheimer's Disease and mood disorders.

DETAILED DESCRIPTION OF THE INVENTION

The object of the present invention is to provide a salt of the compound of 2-hydroxy -3-[5-(morpholin-4-ylmethyl)pyridin-2-yl]1H-indole-5-carbonitrile (compound (I)), namely the 2-hydroxy-3-[5-(morpholin-4-ylmethyl)pyridin-2-yl] 1H-indole-5-carbonitrile citrate,

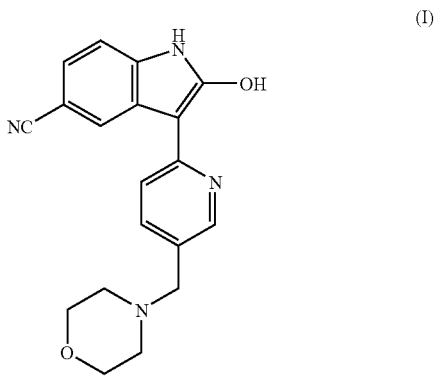

(I)

having a selective inhibiting effect at GSK3, a good bioavailability, a good solubility and a low hygroscopicity which making it suitable to be formulated into pharmaceutical formulations.

The citrate salt of the compound of formula (I) according to the present invention have surprisingly been found to show an improved chemical stability over the hydrochloride salt of 2-hydroxy-3-[5-(morpholin-4-ylmethyl)pyridin-2-yl]1H-indole-5-carbonitrile prepared as described in WO 03/082853 which makes it particularly suitable to be formulated into pharmaceutical formulations.

In the formulation of pharmaceutical formulations, it is important for the pharmaceutically acceptable compound (the active drug compound) to be in a form in which it can be conveniently handled and processed. This is of importance, not only form the point of view of obtaining commercially viable manufacturing process, but also from the point of view of subsequent manufacture of pharmaceutical formulations comprising the active drug compound.

Chemical stability, solid state stability, and "shelf-life" of the active ingredients are also very important factors. The drug compound and formulations containing it should be capable of being effectively stored over appreciable periods of time, without exhibiting a significant change in physico-chemical characteristics of the active component, e.g. its chemical composition, density, hygroscopicity and solubility.

The term "chemical stability" means that the compound can be stored in an isolated form, or in the form of a formulation in which it is provided in admixture with pharmaceutically acceptable carriers, diluents or adjuvants (e.g., in an oral dosage form, such as tablet, capsule, etc.), under normal storage conditions, with little or no chemical degradation or decomposition.

Thus, in the manufacture of commercially viable and pharmaceutically acceptable drug formulations it is important, wherever possible, to provide the drug compound in a substantially crystalline and stable form.

As used herein, the term "substantially crystalline" means at least about 50% crystalline and ranging up to 100% crystalline. The present invention provides 2-hydroxy-3-[5-(morpholin-4-ylmethyl)pyridin-2-yl]1H-indole-5-carbonitrile citrate that is at least about 50% crystalline, at least about 60% crystalline, at least about 70% crystalline, at least about 80% crystalline, at least about 90% crystalline, at least about 95% crystalline, at least about 98% crystalline, or about 100% crystalline in form.

Pharmaceutical Formulations

According to one aspect of the present invention there is provided a pharmaceutical formulations comprising the citrate salt of the compound (I), 2-hydroxy-3-[5-(morpholin-4-ylmethyl)pyridin-2-yl]1H-indole-5-carbonitrile, for use in the prevention and/or treatment of conditions associated with glycogen synthase kinase-3.

The formulation may be in a form suitable for oral administration, for example as a tablet, for parenteral injection as a sterile solution or suspension, for local administration in a body cavity or in a bone cavity, for example as a sterile injection solution or suspension.

In general the above formulation may be prepared in a conventional manner using pharmaceutically carriers or diluents. Suitable daily doses of the salt of the compound of formula (I) in the treatment of a mammal, including man, are approximately 0.01 to 250 mg/kg bodyweight at peroral administration and about 0.001 to 250 mg/kg bodyweight at parenteral administration. The typical daily dose of the active ingredients varies within a wide range and will depend on various factors such as the relevant indication, the route of administration, the age, weight and sex of the patient and may be determined by a physician.

For the veterinary use the amounts of different components, the dosage form and the dose of the medicament may vary and will depend on various factors as for example the individual requirement of the animal treated.

A pharmaceutically acceptable salt the compound of formula (I), can be used on its own but will usually be administered in the form of a pharmaceutical formulation in which the formula (I) compound salt (active ingredient) is in association with a pharmaceutically acceptable diluent or carrier. Dependent on the mode of administration, the pharmaceutical formulation may comprise from 0.05 to 99% w (percent by weight), for example from 0.10 to 50% w, of active ingredient, all percentages by weight being based on total composition.

A diluent or inert carrier includes water, aqueous poly (ethylene glycol), magnesium carbonate, magnesium stearate, talc, a sugar (such as lactose), pectin, dextrin, starch, tragacanth, microcrystalline cellulose, methyl cellulose, sodium carboxymethyl cellulose or cocoa butter.

A formulation of the invention can be in tablet or injectable form. The tablet may additionally comprise a disintegrant and/or may be coated (for example with an enteric coating or coated with a coating agent such as hydroxypropyl methylcellulose).

The invention further provides a process for the preparation of a pharmaceutical formulation of the invention which comprises mixing a pharmaceutically acceptable salt of the compound of formula (I), as hereinbefore defined, with a pharmaceutically acceptable diluent or inert carrier.

An example of a pharmaceutical formulation of the invention is an injectable solution containing a compound of the invention, or a pharmaceutically acceptable salt, as hereinbefore defined, and sterile water, and, if necessary, either sodium hydroxide or hydrochloric acid to bring the pH of the final formulation to about pH 5, and optionally a surfactant to aid dissolution.

An example of a suitable formulation is a liquid solution comprising 2-hydroxy-3-[5-(morpholin-4-ylmethyl)pyridin-2-yl]1H-indole-5-carbonitrile citrate 5.0% mg/mL dissolved in pure water to 100%.

Medical Uses

Surprisingly, it has been found that the new 2-hydroxy-3-[5-(morpholin-4-ylmethyl)pyridin-2-yl]1H-indole-5-carbonitrile citrate defined in the present invention, are well suited for inhibiting glycogen synthase kinase-3 (GSK3). Accordingly, said compound of the present invention is expected to be useful in the prevention and/or treatment of conditions associated with glycogen synthase kinase-3 activity, i.e. the compounds may be used to produce an inhibitory effect of GSK3 in mammals, including man, in need of such prevention and/or treatment.

GSK3 is highly expressed in the central and peripheral nervous system and in other tissues. Thus, it is expected that compound of the invention is well suited for the prevention and/or treatment of conditions associated with glycogen synthase kinase-3 in the central and peripheral nervous system. In particular, the compound of the invention is expected to be suitable for prevention and/or treatment of conditions associated with cognitive disorders and predemented states, especially dementia, Alzheimer's Disease (AD), Cognitive Deficit in Schizophrenia (CDS), Mild Cognitive Impairment (MCI), Age-Associated Memory Impairment (AAMI), Age-Related Cognitive Decline (ARCD) and Cognitive Impairement No Dementia (CIND), diseases associated with neurofibrillar tangle pathologies, Frontotemporal dementia (FTD), Frontotemporal dementia Parkinson's Type (FTDP), progressive supranuclear palsy (PSP), Pick's Disease, Niemann-Pick's Disease, corticobasal degeneration (CBD), traumatic brain injury (TBI) and dementia pugilistica.

One embodiment of the invention relates to the prevention and/or treatment of Alzheimer's Disease, especially the use in the delay of the disease progression of Alzheimer's Disease.

Other conditions are selected from the group consisting of Down's syndrome, vascular dementia, Parkinson's Disease (PD), postencephelatic parkinsonism, dementia with Lewy bodies, HIV dementia, Huntington's Disease, amyotrophic lateral sclerosis (ALS), motor neuron diseases (MND, Creuztfeld-Jacob's disease and prion diseases.

Other conditions are selected from the group consisting of attention deficit disorder (ADD), attention deficit hyperactivity disorder (ADHD) and affective disorders, wherein the affective disorders are Bipolar Disorder including acute mania, bipolar depression, bipolar maintenance, major depressive disorders (MDD) including depression, major depression, mood stabilization, schizoaffective disorders including schizophrenia, and dysthymia.

Other conditions are selected from the group consisting of Type I diabetes, Type II diabetes, diabetic neuropathy, alopecia and inflammatory diseases.

One embodiment of the invention relates to the prevention and/or treatment of bone-related disorders in mammals.

Another aspect of the invention is directed to the use of 2-hydroxy-3-[5-(morpholin-4-ylmethyl)pyridin-2-yl]1H-indole-5-carbonitrile citrate in the prevention and/or treatment of to treat osteoporosis in mammals.

One aspect of the invention is directed to the use of 2-hydroxy-3-[5-(morpholin-4-ylmethyl)pyridin-2-yl]1H-indole-5-carbonitrile citrate to promote and/or increase bone formation in mammals.

One aspect of the invention is directed to the use of 2-hydroxy-3-[5-(morpholin-4-ylmethyl)pyridin-2-yl]1H-indole-5-carbonitrile citrate to increase bone mineral density in mammals.

Another aspect of the invention is directed to the use of 2-hydroxy-3-[5-(morpholin-4-ylmethyl)pyridin-2-yl]1H-indole-5-carbonitrile citrate to reduce the rate of fracture and/or increase the rate of fracture healing in mammals.

Another aspect of the invention is directed to the use of 2-hydroxy-3-[5-(morpholin-4-ylmethyl)pyridin-2-yl]1H-indole-5-carbonitrile citrate to increase cancellous bone formation and/or new bone formation in mammals.

The dose required for the therapeutic or preventive treatment of a particular disease or a particular condition will necessarily be varied depending on the host treated, the route of administration and the severity of the illness or injury being treated.

The present invention relates also to the use of 2-hydroxy-3-[5-(morpholin-4-ylmethyl)pyridin-2-yl]1H-indole-5-carbonitrile citrate in the manufacture of a medicament for the prevention and/or treatment of conditions associated with glycogen synthase kinase-3.

In the context of the present specification, the term "therapy" also includes "prevention" unless there are specific indications to the contrary. The terms "therapeutic" and "therapeutically" should be construed accordingly.

The invention also provides for a method of treatment and/or prevention of conditions associated with glycogen synthase kinase-3 comprising administering to a mammal, including man or animal in need of such treatment and/or prevention a therapeutically effective amount of the 2-hydroxy-3-[5-(morpholin-4-ylmethyl)pyridin -2-yl]1H-indole-5-carbonitrile citrate.

Method of Salt Formation

The formation of the salt of the compound of formula (I), 2-hydroxy-3-[5-(morpholin-4-ylmethyl)pyridin-2-yl]1H-indole-5-carbonitrile citrate salt, may be prepared by mixing 2-hydroxy-3-[5-(morpholin-4-ylmethyl)pyridin-2-yl]1H-indole -5-carbonitrile with citric acid in the presence of a solvent. The equivalent of citric acid may vary between 1 and 3 mole equivalents.

The reaction may be performed in a solvent, suitable solvents are ethers such as 1,4-dioxane, diethyl ether or alcohols such as methanol, ethanol, propanol, or ketones such as acetone, isobutylmethylketone, or acetates such as ethyl acetate, butylacetate, or organic acids such as acetic acid, or mixtures thereof, optionally using water as an additive. The solvent, which is a mixture of ethanol and water or acetic acid is suitable.

The total volume of solvents used may vary between 1 (v/w) to 100 (v/w) volume parts per weight of starting material, preferably between 10 (v/w) and 45 (v/w) volumes parts per weight of starting material. The temperature of the reaction may be between −30 and +150° C., preferably between −5° C. and +100° C.

Pure compound of formula (I), 2-hydroxy-3-[5-(morpholin-4-ylmethyl)pyridin-2-yl]1H -indole-5-carbonitrile citrate, may be obtained by crystallising with or without an additive in suitable solvents to obtain a crystalline solid having a purity of about 95% and preferably about 98%

Another object of the present invention is the process for salt formation as described above.

WORKING EXAMPLE

The following examples will describe, but not limit, the invention.

Example 1

2-Hydroxy-3-[5-(morpholin-4-ylmethyl)pyridin-2-yl]1H-indole-5-carbonitrile citrate salt 2-Hydroxy-3-[5-(morpholin-4-ylmethyl)pyridin-2-yl]1H-indole-5-carbonitrile (5.14 kg, 15.4 mol) was suspended in ethanol (54 L) at room temperature. The suspension was heated to an inner temperature of 70° C. and a solution of citric acid (3.424 kg, 17.82 mol) in water (103 L) was added keeping the inner temperature above 65° C. The mixture was heated to reflux. After this the resulting solution was mixed with activated charcoal (0.412 kg) and reflux continued for 3.5 h after which the reaction mixture was clear filtered at 83° C. followed by cooling to room temperature over 20 h. After filtration the precipitate was washed twice with a cold mixture of ethanol/water (6.9 L/13.7 L). Drying under vacuum at 50° C. gave 6.648 kg, 82.2% yield of 2-hydroxy-3-[5-(morpholin-4-ylmethyl)pyridin-2-yl]1H-indole-5-carbonitrile citrate having a purity of at least 98%. The palladium content was less than 1 ppm and the zinc content was lower than 10 ppm. $^1$H NMR (d6-DMSO, 400 MHz) δ 14.8 (br s, 1 H), 10.98 (s, 1H), 8.1 (s 1H), 7.55 (m, 3H), 7.31 (d, 1 H), 7.02 (d, 1H), 3.6 (s, 4H), 3.45 (m, 2H), 2.75 (ap d, 2H), 2.65 (ap d, 2H), 2.47 (s, 4H) ppm; $^{13}$C NMR (d6-DMSO, 400 MHz) δ 174.9, 171.3, 168.7, 148.4, 142.1, 137.1, 136.4, 125.2, 124.1, 121.1, 121.0, 118.8, 118.4, 101.4, 84.6, 72.3, 65.7, 58.0, 52.5, 42.9 ppm; MS (ES) m/z [M$^+$+1] 335.

The crystals were analysed by X-ray powder diffraction (XRPD). The diffractogram of Form A shows the following d-values given in Angstrom and relative intensities: 12.7 (vs), 7.6 (w), 6.8 (vs), 6.3 (s), 5.9 (w), 5.7 (m), 5.1 (m), 4.87 (w), 4.57 (m), 4.38 (s), 4.23 (s), 4.16 (w), 4.07 (m), 3.80 (w), 3.69 (m), 3.65 (w), 3.41 (m), 3.37 (w), 3.32 (m), 3.17 (m), 3.12 (m), 2.88 (w), 2.86 (m), 2.78 (w), 2.65 (w), 2.50 (w), 2.45 (w).

The significant d-values given in Angstrom and relative intensities are: 12.7 (vs), 6.8 (vs), 6.3 (s), 4.38 (s), 4.23 (s), 3.41 (m).

Crystallinity of 2-hydroxy-3-[5-(morpholin-4-ylmethyl)pyridin -2-yl]1H-indole-5-carbonitrile citrate were analyzed using X-ray powder diffraction (XRPD) as described below:

The peaks, identified with d-values calculated from the Bragg formula and intensities, have been extracted from the diffractogram of crystalline citrate salt. Only the main peaks, that are the most characteristic, significant, distinct and/or reproducible, have been tabulated, but additional peaks can be extracted, using conventional methods, from the diffractogram. The presence of these main peaks, reproducible and within the error limit, is for most circumstances sufficient to establish the presence of said crystalline salt. The relative intensities (rel.int.) are less reliable and instead of numerical values the following definitions are used:

| | |
|---|---|
| vs (very strong): | >60% rel int. |
| s (strong): | 23-60% rel int. |
| m (medium): | 9-23% rel int. |
| w (weak): | 4-9% rel int. |
| vw (very weak): | <4% rel int. |

X-ray diffraction analyses were performed using a PANalytical X'Pert Pro MPD diffractometer for 64 minutes from 1 to 40° 2θ with and without internal standard reference. The 2θ angles were corrected with regard to the standard values whereafter calculation into d-values (distance values) was done. The d-values may vary in the range ±2 on the last given decimal place. The sample preparation was performed according to standard methods, for example those described in Giacovazzo, C. et al (1995), Fundamentals of Crystallography, Oxford University Press; Jenkins, R. and Snyder, R. L. (1996), Introduction to X-Ray Powder Diffractometry, John Wiley & Sons, New York; Bunn, C. W. (1948), Chemical Crystallography, Clarendon Press, London or Klug, H. P. & Alexander, L. E. (1974), X-ray Diffraction Procedures, John Wiley and Sons, New York.

Pharmacology

Determination of ATP competition in Scintillation Proximity GSK3β Assay.

GSK3β Scintillation Proximity Assay.

The competition experiments were carried out in duplicate with 10 different concentrations of the inhibitor in clear-bottom microtiter plates (Wallac, Finland). A biotinylated peptide substrate, Biotin-Ala-Ala-Glu-Glu-Leu-Asp-Ser-Arg-Ala-Gly-Ser($PO_3H_2$)-Pro-Gln-Leu (AstraZeneca, Lund), was added at a final concentration of 1 μM in an assay buffer containing 1 mU recombinant human GSK3β (Dundee University, UK), 12 mM morpholinepropanesulfonic acid (MOPS), pH 7.0, 0.3 mM EDTA, 0.01% β-mercaptoethanol, 0.004% Brij 35 (a natural detergent), 0.5% glycerol and 0.5 μg BSA/25 μl. The reaction was initiated by the addition of 0.04 μCi [γ-$^{33}$P]ATP (Amersham, UK) and unlabelled ATP at a final concentration of 1 μM and assay volume of 25 μl. After incubation for 20 minutes at room temperature, each reaction was terminated by the addition of 25 μl stop solution containing 5 mM EDTA, 50 μM ATP, 0.1% Triton X-100 and 0.25 mg streptavidin coated Scintillation Proximity Assay (SPA) beads (Amersham, UK). After 6 hours the radioactivity was determined in a liquid scintillation counter (1450 Micro-Beta Trilux, Wallac). The inhibition curves were analysed by non-linear regression using GraphPad Prism, USA. The $K_m$ value of ATP for GSK3β, used to calculate the inhibition constants ($K_i$) of the compound, was 20 μM.

The following abbreviations have been used:
MOPS Morpholinepropanesulfonic acid
EDTA Ethylenediaminetetraacetic acid
BSA Bovin Serum Albumin
ATP Adenosine Triphosphate
SPA Scintillation Proximity Assay
GSK3 Glycogen synthase kinase 3

Results

The $K_i$ value for 2-hydroxy-3-[5-(morpholin-4-ylmethyl)pyridin-2-yl]1H-indole-5-carbonitrile citrate of the present invention are in the range of 0.001 nM to 300 nM.

Chemical Stability
Hygroscopicity
Dynamic Vapour Sorption Analysis (DVS)

The studies were undertaken using Dynamic Vapour Sorption Appararatus (DVS, Surface Measurement Systems, London UK). The apparatus consists of Cahn micobalance housed inside a temperature-controled cabinet. All experiments were performed at 25° C. The DVS was used to characterize the moisture uptake (w/w %) at different relative humidities (RH). Samples (5-10 mg) were weighed directly into the DSV sample cup and exposed to different relative humidities.

Results

|  | Relative humidities (RH) | | |
| --- | --- | --- | --- |
| Sample | 40% | 60% | 80% |
| HCl | 8.7 | 11.5 | 13.0 |
| Citrate | 7.1 | 7.6 | 8.0 |

It is clear from the results above that the citrate salt of 2-hydroxy-3-[5-(morpholin-4-ylmethyl)pyridin-2-yl]1H-indole-5-carbonitrile shows a lower hygroscopicity than the hydrochloride salt thereof and is thus more suitable for preparing pharmaceutical formulations.

Solution Stability

An isotonic solution of the citrate and the hydrochloride salt of 2-hydroxy-3-[5-(morpholin-4-ylmethyl)pyridin-2-yl]1H-indole-5-carbonitrile (0.1 mg/ml), respectively, containing ascorbic acid (0.5% (w/v)) and adjusted to pH 2 and 4 with HCL (2M) and NaOH (2M) were prepared and stored for four weeks between 4 to 8° C.

Method for Analysis.

| HPLC: | HP1100 |
| --- | --- |
| Column: | Symmetry C18, 5 μm, 3.9 × 150 mm |
| Stop time: | 5 min |
| Wave length: | 361 nm |
| Injection volume: | 10 μl |
| Flow: | 1 ml/min |

Mobile phase 0.05 M phosphate buffer pH 3: acetonitrile: phosphate buffer (80:20).

Results

After analysis it was shown that the hydrochloride salt of 2-hydroxy-3-[5-(morpholin-4-ylmethyl)pyridin-2-yl]1H-indole-5-carbonitrile degraded by approx. 10% whilst the citrate salt of 2-hydroxy-3-[5-(morpholin-4-ylmethyl)pyridin-2-yl]1H-indole-5-carbonitrile was stable and showed no degradation products.

Photo Stability of Bulk Substance

The free base and the corresponding hydrochloride salt and citrate salt of 2-hydroxy-3-[5-(morpholin-4-ylmethyl)pyridin-2-yl]1H-indole-5-carbonitrile were tested for light stability in a Suntest CPS+ cabinet. The exposure was 250 Wh/m$^2$ and 1.2 million lux hours over 29 hours.

Results

| Exposure time (hours) | HCl | Citrate | Free base |
| --- | --- | --- | --- |
| 0 | 97.5 | 99.0 | 96.6 |
| 29 control sample (stored in the dark) | 97.7 | 99.1 | 96.1 |
| 29 | 89.0 | 98.1 | 83.8 |

It is clear from the results above that the citrate salt of 2-hydroxy-3-[5-(morpholin-4-ylmethyl)pyridin-2-yl]1H-indole-5-carbonitrile shows a much higher photo stability than both the hydrochloride salt and the free base thereof and thus are more suitable for preparing pharmaceutical formulations.

CONCLUSION

It is clear from the comparisons between the free base, the hydrochloride and the citrate salt of 2-hydroxy-3-[5-(morpholin-4-ylmethyl)pyridin-2-yl]1H-indole-5-carbonitrile that the citrate salt thereof is more stable against decomposition compared to the hydrochloride salt and thus more suitable for preparing pharmaceutical formulations.

The invention claimed is:
1. A salt, which is 2-hydroxy-3[5-(morpholin-4-ylmethyl)pyridin-2-yl]1H-indole-5-carbonitrile citrate.
2. A salt according to claim 1 in substantially crystalline form.
3. A salt according to claim 1 or 2, which is a Form A characterized by the X-ray powder diffraction d-values and relative intensity 12.7(vs), 6.8(vs), 6.3(s), 4.38(s), 4.23(s) and 3.41(m) Å.
4. A process for the preparation of 2-hydroxy-3-[5-(morpholin-4-ylmethyl)pyridin-2-yl]1H-indole-5-carbonitrile citrate according to claim 1 which comprises reacting 2-hydroxy-3-[5-(morpholin-4-ylmethyl)pyridin-2-yl]1H-indole-5-carbonitrile with citric acid in a solvent.
5. The process according to claim 4, wherein the solvent used is selected from the group consisting of ethers, alcohols, ketones, acetates or organic acids, or mixtures thereof, optionally using water as an additive.
6. A process according to claim 5 wherein the solvent is a mixture of ethanol and water or acetic acid.
7. A process according to claim 4 wherein said process is carried out at a temperature of between −5° C. and +100° C.
8. A pharmaceutical formulation comprising as active ingredient a therapeutically effective amount of the salt according to claim 1, optionally in association with diluents, recipients or inert carriers.

* * * * *